(12) United States Patent
Hader

(10) Patent No.: US 11,911,205 B2
(45) Date of Patent: Feb. 27, 2024

(54) ADVANCED MEDICAL IMAGING IN DISTRIBUTED SETUP

(71) Applicant: Siemens Healthcare GmbH, Erlangen (DE)

(72) Inventor: Sandra Hader, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 417 days.

(21) Appl. No.: 17/024,822

(22) Filed: Sep. 18, 2020

(65) Prior Publication Data
US 2021/0093285 A1 Apr. 1, 2021

(30) Foreign Application Priority Data
Sep. 27, 2019 (EP) ..................................... 19199989

(51) Int. Cl.
*A61B 6/00* (2006.01)
*G16H 40/67* (2018.01)
*G16H 10/60* (2018.01)
*G16H 30/00* (2018.01)
*A61B 6/03* (2006.01)

(52) U.S. Cl.
CPC .............. *A61B 6/548* (2013.01); *A61B 6/032* (2013.01); *G16H 10/60* (2018.01); *G16H 30/00* (2018.01); *G16H 40/67* (2018.01)

(58) Field of Classification Search
CPC ........ A61B 6/548; A61B 6/032; G16H 10/60; G16H 30/00; G16H 40/67; G16H 40/20; G16H 80/00; G16H 40/63; G16H 30/20
See application file for complete search history.

(56) References Cited

U.S. PATENT DOCUMENTS

| | | |
|---|---|---|
| 2003/0083563 A1 | 5/2003 | Katsman et al. |
| 2009/0005669 A1 | 1/2009 | Schmidt et al. |
| 2013/0331664 A1 | 12/2013 | Gilad-Gilor |
| 2019/0269386 A1 | 9/2019 | Raju et al. |
| 2021/0098125 A1* | 4/2021 | Lautenschlaeger .... G16H 30/40 |
| 2023/0187087 A1* | 6/2023 | Chamarthi ............. G16H 80/00 705/2 |

FOREIGN PATENT DOCUMENTS

| | | |
|---|---|---|
| CN | 103717127 A | 4/2014 |
| CN | 206214122 U | 6/2017 |

(Continued)

*Primary Examiner* — David P Porta
*Assistant Examiner* — Gisselle M Gutierrez
(74) *Attorney, Agent, or Firm* — Harness, Dickey & Pierce, P.L.C.

(57) ABSTRACT

A computer-implemented method is for performing at least one medical imaging procedure using an imaging modality. The medical imaging procedure is performed under remote supervision. An embodiment of the method includes acquiring with a computing unit data on the medical imaging procedure to be performed; acquiring with the computing unit data on at least one expert operator, located at a workplace remote from the imaging modality; matching data on the medical imaging procedure with data on the expert operator; assigning at least one expert operator to the medical imaging procedure based on the matching; and providing a communication channel between the imaging modality and the remote workplace.

17 Claims, 3 Drawing Sheets

(56) References Cited

FOREIGN PATENT DOCUMENTS

| | | |
|---|---|---|
| CN | 107273700 A | 10/2017 |
| CN | 107610754 A | 1/2018 |
| CN | 109313931 A | 2/2019 |
| CN | 109963514 A | 7/2019 |
| CN | 110232967 A | 9/2019 |
| WO | WO-2015059698 A1 | 4/2015 |

* cited by examiner

| ROW 1 TIME | ROW 2 CT 1 | ROW 3 CT 2 | ROW 4 MR 1 | ROW 5 MR 2 |
|---|---|---|---|---|
| 8.00 - 8.15 | Müller, G. Spine EXO 1 | Tischler, K. Abdomen EXO 1 | Fahner, F. Cardio EXO 3 | Mayer, B. Head EXO 1 |
| 8.30 - 8.45 | Fischer, O. Abdomen - | Schreiner, P. Head EXO 1 | | Lindner, K. Abdomen EXO 1 |
| 9.00 - 9.15 | Schneider, R. Head EXO | Maurer, J. Knee - | Hinze, K. Knee EXO 1 | Bercht, T. Onco Whole Body EXO 2 |
| 9.30 - 9.45 | - | - | Eller, M. Onco Whole Body EXO 2 | |
| 10.00 - 10.15 | - | - | | - |

} SCH

ADVANCED MEDICAL IMAGING IN DISTRIBUTED SETUP

PRIORITY STATEMENT

The present application hereby claims priority under 35 U.S.C. § 119 to European patent application number EP19199989.5 filed Sep. 27, 2019, the entire contents of which are hereby incorporated herein by reference.

FIELD

Embodiments of the invention generally relate to advanced medical imaging in a distributed setup.

BACKGROUND

Modern medical imaging workflows require profound and experienced technical know-how on a 24/7 basis. Especially, complex imaging procedures using a medical imaging modality like a computed tomography or magnetic resonance tomography system require deep understanding of functionality and the underlying image generation process for individual imaging modalities.

Currently, performing an imaging procedure would be based on scheduling a scanner room, an imaging modality therein and one or even two technologists/medical experts likewise present in or close to the scanner room for the duration of the whole imaging procedure.

However, healthcare providers are more and more confronted with a decreasing on-site availability of experienced technologists or radiographers. Particularly, remote or rural locations suffer from shortage of well-educated and trained medical staff to locally perform medical imaging procedures.

This causes long and uncomfortable waiting or travel times for patients, or even both. This may even cause a danger for patient health.

Furthermore, while medical imaging procedures require expert staff input as regards e.g. planning of the required imaging protocol or patient positioning, especially time-consuming measurements take a lot of valuable working time from a technical expert when considering his physical presence for just monitoring the patient in the course of a measurement or the measurement as such. This causes workflow inefficiencies.

SUMMARY

At least one embodiment of the present invention provides alternative devices and/or methods which allow for a flexible and on-demand allocation of technical expert knowledge as needed for conducting medical imaging procedures.

Embodiments are directed to a method for performing at least one medical imaging procedure using an imaging modality, wherein the medical imaging procedure is performed under remote supervision; a corresponding system; a corresponding computer-program product and computer-readable medium. Alternative and/or preferred embodiments are object of the claims.

In the following the technical solution according to embodiments of the present invention is described with respect to the claimed apparatuses as well as with respect to the claimed methods. Features, advantages or alternative embodiments described herein can likewise be assigned to other claimed objects and vice versa. In other words, claims addressing the inventive method can be improved by features described or claimed with respect to the apparatuses. In this case, e.g. functional features of the method are embodied by objective units or elements of the apparatus.

Accordingly, a first embodiment of the present invention is directed to a computer-implemented method for performing at least one medical imaging procedure using an imaging modality. The medical imaging procedure is performed under remote supervision. The method comprises:

acquiring, with a computing unit, data on the medical imaging procedure to be performed, acquiring, with the computing unit, data on at least one expert operator located at a workplace remote from the imaging modality, matching, with the computing unit, the data on the medical imaging procedure with the data on the expert operator, assigning, with the computing unit, at least one expert operator to the medical imaging procedure based on the matching, and providing a communication channel between the imaging modality and the remote workplace.

According to another embodiment of the present invention, the communication channel between imaging modality and remote workplace is configured to enable remote setting of imaging parameters at the imaging modality by the expert operator and/or verbal and/or written or textual communication via the imaging modality and the remote workplace, particularly between the local and the expert operator.

A further embodiment of the present invention is directed to a system for performing at least one medical imaging procedure using an imaging modality, wherein the medical imaging procedure is performed under remote supervision. The system comprises the following units:

at least one imaging modality, at least one workplace remote from the imaging modality, a computing unit configured for acquiring data on the medical imaging procedure to be performed, acquiring data on at least one expert operator, located at a workplace remote from the imaging modality, matching data on the medical imaging procedure with data on the expert operator, and assigning at least one expert operator to the medical imaging procedure based on the matching.

A further embodiment of the present invention is directed to a computer program product comprising program elements which induce a computing unit of a system for performing at least one medical imaging procedure using an imaging modality, to perform the steps according to at least one embodiment of the inventive method, when the program elements are loaded into a memory of the computing unit, wherein the medical imaging procedure is performed under remote supervision.

A further embodiment of the present invention is directed to a computer-readable medium on which program elements are stored that are readable and executable by a computing unit of a system for performing at least one medical imaging procedure using an imaging modality, in order to perform steps of at least one embodiment of the inventive method, when the program elements are executed by the computing unit, wherein the medical imaging procedure is performed under remote supervision.

BRIEF DESCRIPTION OF THE DRAWINGS

Characteristics, features and advantages of the above described invention, as well as the manner they are achieved, become clearer and more understandable in the light of the following description and embodiments, which will be described in detail with respect to the figures. This following description does not limit the invention on the contained embodiments. Same components or parts can be labeled with the same reference signs in different figures. In general, the figures are not to scale. In the following.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Accordingly, a first embodiment of the present invention is directed to a computer-implemented method for performing at least one medical imaging procedure using an imaging modality. The medical imaging procedure is performed under remote supervision.

Remote supervision may comprise remote interaction with and/or remote controlling of a medical imaging modality, e.g. starting and/or stopping a medical imaging procedure, setting and/or adjusting medical imaging parameters for a selected imaging protocol, interaction related to patient positioning or the like. Remote supervision may thus comprise data exchange between a remote workplace and the imaging modality, wherein a communication channel is required. Remote supervision may also comprise verbal and/or textual or video data exchange and or data transfer between a remote expert operator and a local operator and/or the patient under examination. In other words, data exchange and/or data transfer may occur bidirectionally.

At least one embodiment of the invention is based on the finding, that medical/technical expert knowledge does not need to be locally present at the site of a medical imaging procedure but may advantageously be provided remotely at the requested time.

Advantageously, according to at least one embodiment of the method, at least one, preferably more than one medical imaging procedures are performed. In case of more than one medical imaging procedure, more than one imaging modalities may be used. With other words, each imaging procedure may be conducted with a different imaging modality. The plurality of imaging procedures may be performed consecutively. At least two imaging procedures may be performed at the same time or at least partially in an overlapping manner.

An imaging modality preferably corresponds to a medical imaging modality. A medical imaging modality is to be understood as a system used to generate or produce medical images of at least a body part of a patient. With other words, a medical imaging procedure corresponds to the process of acquiring or generating medical image data for a body part of a patient. For example, a medical imaging modality may be a computed tomography system, a magnetic resonance tomography system, an angiography (or C-arm X-ray) system, a positron-emission tomography system or the like.

Specifically, computed tomography (CT) is a widely used imaging method and makes use of "hard" X-rays produced and detected by a specially rotating instrument. The produced medical images are called CT-scans and serve to present the internal anatomical structures in cross sections perpendicular to the axis of the patient's body. Magnetic Resonance Imaging (MRI) is an advanced diagnostic technique which makes use of the effect a magnetic field impacts on movements of protons. In MRI machines, the detectors are antennas and the signals are analyzed by a computer creating detailed images of the internal structures in any section of the human body.

In at least one embodiment, the method comprises a plurality of steps.

A first step is directed to acquiring, with a computing unit, data on the medical imaging procedure to be performed. Preferably data for a plurality, i.e. more than one, medical imaging procedures are acquired. The data on the at least one medical imaging procedure may be adapted to better describe the medical imaging procedure and characterize its specific requirements. The data on the medical imaging procedure may preferably serve to distinguish different medical imaging procedures from each other. The medical imaging procedures taken into account may preferably relate to a certain time shift, e.g. in a radiology workflow. The medical imaging procedures may relate to different imaging modalities as well as different medical sites the imaging modalities are located at. A medical site is to be understood as a medical facility like a hospital, a radiology institution or a radiological department. A medical site comprises at least one medical imaging apparatus or system for conducting medical imaging procedures. Preferably, several medical imaging systems are located at a medical site.

Another step is directed to acquiring, with the computing unit, data on at least one expert operator, located at a workplace remote from the imaging modality and/or the medical sites. With other words, the expert operator may have access to the remote workplace or may be based at the remote workplace. This means that the expert operator may be present at the location of the remote workplace or may remotely access the remote workplace from another location. Preferably data for a plurality, i.e. more than one, expert operator are acquired. The expert operator may be understood as medical and/or technical expert person, who is well trained and/or highly experienced in conducting and guiding medical imaging procedures. Typically, expert knowledge and experience level is specific for only one or a limited number of medical imaging procedures and/or corresponding imaging modalities. With other words, a workplace provides a pool of expert operators or specific technical/medical expertise and knowledge.

The expert operator is further characterized in that he or she is located remote from at least one of the imaging modalities. With other words, in a system with more than one imaging modalities at different medical sites, the expert operator may be located at the medical site of one of the imaging modalities, but remote from the other medical sites of the system. Alternatively, the expert operator is located at a completely different location. The expert operator is further characterized in that he or she can remotely operate at least one, preferably more than one, most preferably consecutively more than one of the imaging modalities in the course of a respective imaging procedure. The data on the at least one remote expert operator may serve to identify the expert operator and/or to distinguish the expert operator from other remote expert operators as regards their individual medical and/or technical expert competences and/or their availability. The at least one expert operator may be located at only one remote workplace. Alternatively, the expert operator may have access to more than one, i.e. numerous different remote workplaces which are preferably remote from the medical site of the imaging modality.

According to a preferred embodiment of the present invention, any of the steps of acquiring data comprises requesting data from at least one database. The steps of acquiring data may comprise sending a request for the relevant information to a data source, e.g. a database, a local or central server, a hospital or radiology information system (RIS/HIS) or the like. Alternatively, the data processed with the inventive method may be provided in a push-manner, without the need for an initial request.

Data on the at least one imaging procedure may preferably be stored in a database or data repository as part of a RIS or HIS scheduling system or module. Data on the expert operator may be stored in an expert operators' database. An expert operators' database may comprise data on expert operators of one or several remote workplaces and may thus be a workplace-specific or central database. Data on at least one patient or a respective medical condition may preferably be stored in a patient database or data repository repository/database, especially as part of a respective electronic patient or health record file of a medical facility. The step of acquiring or retrieving data may also comprise text or speech file analysis contained in the electronic patient record, e.g. referrals or prior reports. This analysis may comprise optical character recognition (OCR) techniques and/or semantic analysis.

Another method step is directed to matching with the computing unit data on the medical imaging procedure with data on the expert operator. This means at least parts of the data related to the medical imaging procedure and at least parts of the data related to the expert operator are matched. With other words, the step of matching identifies a conformity or compatibility measure between a medical imaging procedure and an expert operator. Preferably, the step of matching identifies a plurality of conformity measures for a plurality of imaging procedure-expert pairs based on the acquired data. As an example, one of these conformity measures may include comparing the availability of the expert operator to the scheduled time for performing the medical imaging procedure.

In doing so, at least one embodiment of the inventive method identifies preferable and/or advantageous combinations of expert operators and imaging procedures in the sense that specific technical expertise is fit to specific requirements of an imaging procedure.

The step of matching may comprise binary matching according to preset data combinations or may comprise determination of a compatibility degree relating to a continuous scale. This step of matching may comprise to at least temporarily store the compatibility degree or the conformity measure for individual imaging procedure-expert pairs for further processing.

A further method step is directed to assigning with the computing unit at least one expert operator to the medical imaging procedure based on the matching. This step associates a medical imaging procedure to be performed with the remote expert operator identified during matching to have the highest conformity degree. Accordingly, the step of assigning may further comprise comparing the values of conformity of different imaging procedure-expert pairs to identify the maximum value. This step of assigning may further comprise to store the assignment of expert operator to the corresponding imaging procedure in a scheduling component of a HIS or RIS.

The step of assigning may alternatively comprise not to assign an expert operator to at least one medical imaging procedure, e.g. when the values for the conformity degree are below a predefined threshold or no expert operator is available.

A further step of the method is directed to providing a communication channel between the imaging modality and the remote workplace. With other words, this step establishes an interactive connection between workplace, i.e. the expert operator and the medical imaging modality, which enables real-time interaction between the expert operator and the imaging modality during imaging procedure. The communication channel my preferably be based on virtual networking computing techniques (VNC). Providing the communication channel may comprise a log-in step for the expert operator using a registered ID and password.

In other words, it is an idea of at least one embodiment of the present invention to provide real-time medical and/or technical expert operator guidance and/or control by identifying an expert operator well-fitted to the requested imaging procedure, irrespective of the location of the expert operator or the medical imaging modality used for the imaging procedure. In doing so, the inventive method advantageously waives the physical presence of an expert operator at the location a medical imaging procedure is performed at. The steps of analyzing and/or matching the data on the imaging procedure and the expert operator combine specific requirements of an imaging procedure with the necessary medical/technical expertise available at that time.

According to an embodiment of the present invention, the step of providing the communication channel comprises notifying, with the computing unit, the imaging modality of the assigned expert operator. Notification may be sent to the imaging modality prior to establishing a communication channel. The notification may be sent from the computing unit performing the method steps. Additionally or alternatively, prior notification may be sent to the workplace the expert operator is located at. Notification may further be sent via the respective communication partners, i.e. from computing unit to the imaging modality and from imaging modality to the remote workplace.

According to an embodiment of the present invention, the expert operator is concurrently assigned to more than one imaging procedures and a communication channel is provided between the remote workplace and each respective imaging modality. With other words, based on the matching step, more than one imaging procedures are identified providing a conformity degree value above a predefined threshold. The respective identified imaging modalities may be located at one or a plurality of medical sites. Accordingly, one expert operator remotely attends at least partially and/or intermittently more than one imaging procedure. This embodiment enables effective and thus cost-saving usage of valuable working time of an expert operator. At the same time, quality and thus effectiveness of each of the attended imaging procedures is increased leading to less repeat measurements, higher patient comfort and/or more effective workflow and modality occupancy.

According to another preferred embodiment of the present invention, the more than one imaging procedures are performed at at least two different medical sites, wherein the expert operator is connected to both these medical sites. The embodiment of the invention thus enables flexible provision of expert knowledge irrespective of where the expert operator is located. The at least two different medical sites may both be located remote from the remote workplace, i.e. remote from each other. In Other words, three different locations are involved. However, one of the medical sited may likewise be located at the location of the remote workplace. Here, only two different locations are involved.

Alternatively, the at least two imaging procedures are conducted at the same medical site.

According to an embodiment of the present invention, the data on the at least one expert operator comprises at least one of the following group of data/information
    identification data,
    availability data,
    expert knowledge data.

Identification data may be configured to identify an expert operator among others. Identification data may e.g. comprise name tags, individual acronyms, initials. Availability data may comprise data on regular working hours, time shifts, information on absences of the expert operator. Expert knowledge data may comprise data on technical and/or medical expertise. Expert knowledge data may comprise educational degrees or levels, expertise categories as regards imaging modality type, imaging procedure type, years of working experience or numbers of corresponding examinations conducted or the like.

According to an embodiment of the present invention, the data on the at least one medical imaging procedure comprise at least one of the following group of data/information
    patient related data,
    data on the respective imaging modality (type and availability),
    data on body region or organ of interest,
    initial suspicion data,
    current medical condition data,
    data on timing of the imaging procedure.

Patient related data may be adapted to provide additional information on the patient to be imaged with the imaging procedure, e.g. data on the sex or age of the patient, which may pose specific requirements on the imaging procedure and thus require high level of technical expertise. The data on a medical imaging modality may be adapted to characterize the imaging modality to be applied for the imaging procedure, especially the type of modality, like CT or MRT or a C-arm system or the like. The data on the medical imaging modality may likewise comprise data on the manufacturer, which might likewise impose specific expertise on the operator side. Furthermore, the data may comprise data on the patient's body region or organ of interest, an initial suspicion or data on a patient's current medical condition each data item potentially limiting the applicable imaging protocols or imaging routines.

The degree of conformity reached by conducting an inventive matching step may be higher the more data on the imaging procedure and expert operator are provided and considered for matching.

According to an embodiment of the present invention, the method further comprises a step of acquiring with the computing unit data on at least one local operator, located at the site of the imaging modality. Preferably, data on more than one local operator are acquired.

The local operator, in contrast to the expert operator, is situated at the site for the medical imaging modality used for an imaging procedure. The local operator, in contrast to the expert operator, does not need to have the same level of technical/medical expertise. However, the local operator is responsible for in-situ actions, preferably patient related handling and all patient interaction. With other words, the local operator is responsible for any necessary physical arrangements involved in an imaging procedure, e.g. patient positioning, contrast agent administration, coil positioning, to mention only some examples. Thus, the local operator also needs to be trained well or highly experienced, however, with respect to another field of action.

The step of acquiring may be conducted the same way as laid out before with respect to the expert operator related data. Data on the local operator may be stored in a local operators' database. A local operators' database preferably comprises data on local operators of one medical site and is thus specific for a medical facility.

According to an embodiment of the present invention, the data on the at least one local operator comprises at least one of the following group of data/information
identification data,
availability data,
expert knowledge data.

Identification data may be adapted to identify a local operator among others. Identification data may e.g. comprise name tags, individual acronyms, initials. Availability data may comprise data on regular working hours, time shifts, information on absences of the local operator. Expert knowledge data may comprise educational degrees or levels, expertise categories as regards imaging modality type, imaging procedure type, years of working experience or numbers of corresponding examinations conducted or the like. Another step of the inventive method is directed to matching data on the imaging procedure with data on the local operator. A further step is directed to assigning at least one local operator to the imaging procedure based on the matching.

The matching and assigning steps basically correspond to the ones described with respect to expert operator and imaging procedure previously, albeit being applied on data on the local operator.

Additionally, the step of matching data on the imaging procedure and the local operator may further comprise matching data on at least one expert operator with data on the local operator, thereby further assuring a predefined degree of conformity between the expert and the local operator to be assigned to an imaging procedure. For example, language skills might be matched to guarantee that local and expert operator may communicate during the imaging procedure via the communication channel.

Apart from that, this embodiment may provide as a result that no local expert is assigned to an imaging procedure, e.g. in the case that no in-situ actions are required to be performed by a local operator. In this case, the communication channel according to the inventive method may serve to enable verbal communication between expert operator and patient.

According to another embodiment of the present invention, the communication channel between imaging modality and remote workplace is configured to enable remote setting of imaging parameters at the imaging modality by the expert operator and/or verbal and/or written or textual communication via the imaging modality and the remote workplace, particularly between the local and the expert operator. With other words, the communication channel may provide an internet connection, preferably the communication channel may comprise a voice over internet protocol (VoIP) connection and/or a (text/video or audio) chat connection. The communication channel may thus provide for graphical user interfaces on the side of the remote workplace(s) as well as on the side of the imaging modality. Apart from that, the communication channel may comprise a virtual networking computing techniques (VNC) channel enabling remote control of an imaging modality according to the requirements of an imaging procedure.

According to another embodiment of the present invention, the assignment of the expert operator is adhered to the medical image data generated with the imaging procedure. This measure advantageously provides a record of the expert operator assigned to an imaging procedure. By including information referring to the expert operator involved in the imaging procedure in the medical image data generated while imaging, the expert operator is directly identifiable from viewing the image data. Thus, a radiologist may directly contact an expert operator in case of questions related to the image data or specifics of the imaging procedure. The assignment may be adhered to the image data by introducing an additional meta data tag, e.g. to a respective DICOM image file, wherein the tag may comprise data identifying the expert operator, e.g. personal initials or abbreviations or the like. Alternatively, the assignment of imaging procedure and expert operator may at least temporarily be stored in the RIS or HIS of a medical facility, e.g. in the form of an electronic schedule for all imaging procedures planned for a day and/or a week and/or a month. Here, each entry or field in the schedule may correspond to an imaging procedure which entry may comprise the assigned expert operator. Likewise, the assigned local operator could be stored in the schedule.

A further embodiment of the present invention is directed to a system for performing at least one medical imaging procedure using an imaging modality, wherein the medical imaging procedure is performed under remote supervision. The system comprises the following units:
at least one imaging modality,
at least one workplace remote from the imaging modality,
a computing unit configured for
   acquiring data on the medical imaging procedure to be performed,
   acquiring data on at least one expert operator, located at a workplace remote from the imaging modality,
   matching data on the medical imaging procedure with data on the expert operator, and
   assigning at least one expert operator to the medical imaging procedure based on the matching.

The imaging modality and the remote workplace are configured to provide a communication channel between each other.

The system may comprise only one or more than one, i.e. a plurality of imaging modalities, i.e. at least two imaging modalities. The at least two imaging modalities may be located at different medical sites, however, alternatively at least some of them may be located at the same site, e.g. in a hospital. The imaging modality may comprise an interface or communication unit configured to provide, i.e. establish a communication channel to at least the remote workplace for data exchange, preferably via internet connection. The interface and communication unit may further be adapted to communicate with at least one local and/or central (web-) server, e.g. with a local hospital information system (HIS) or a radiology information system (RIS), a picture archiving and communication system (PACS) or a cloud server.

The system may comprise only one workplace or more than one workplace, i.e. a plurality of workplaces, i.e. at least two workplaces. The workplace according to the present invention is a remote workplace, i.e. the workplace is located remote from at least one of the imaging modalities comprised by the system. With other words, at least one workplace is located at a site different from the site of at least one imaging modality. Thus, the system may comprise a plurality of imaging modalities and a plurality of remote workplaces, wherein at least one workplace may likewise be located at the same site of a first imaging modality, but remote from the site of at least one second imaging modality comprised by the system.

A remote workplace may comprise a user interface unit. A user interface unit may be understood as comprising a display device comprising a display screen such as a workstation or a mobile device. The user interface unit may comprise a communication interface for data exchange with at least one imaging modality, the computing unit, a local server and/or a central (web)server via internet connection. The workplace is further configured to receive or generate and present a visualization of a graphical user interface of at least one imaging modality, e.g. for remote supervision, e.g. for imaging parameter adjustment. Accordingly, the workplace is further adapted to receive expert operator input via an input unit, e.g. for setting an imaging parameter for a medical imaging procedure. Furthermore, the workplace is adapted to provide generate and visualize a graphical user interface for verbal or textual communication between local and expert operator.

Accordingly, the imaging modality also comprises at least one display unit and is adapted to provide and/or generate and visualize a graphical user interface for verbal or textual communication between a local and expert operator.

The computing unit is adapted to implement at least one embodiment of the inventive method for performing at least one medical imaging procedure using an imaging modality, wherein the medical imaging procedure is performed under remote supervision.

Accordingly, the computing unit may comprise an acquisition unit configured to acquire data on at least one medical imaging procedure to be performed, data on at least one expert operator and/or data on at least one local operator. The acquisition unit may be realized in form of an interface unit. The computing unit may further comprise a matching unit configured to match at least partially data on the medical imaging procedure with at least partially data on the expert operator and/or at least partially on the local operator. The computing unit may further comprise an assigning unit configured to assign at last one expert operator and/or at least one local operator to the medical imaging procedure based on the matching. The computing unit may further comprise an initiation unit configured to initiate the setup of a communication channel between the medical imaging modality and the remote workplace.

The computing unit can be realized as a data processing system or as a part of a data processing system. Such a data processing system can, for example, comprise a cloud-computing system, a computer network, a computer, a tablet computer, a smartphone and/or the like. The computing unit can comprise hardware and/or software. The hardware can be, for example, a processor system, a memory system and combinations thereof. The hardware can be configurable by the software and/or be operable by the software. Generally, all units, sub-units or modules of the computing unit may be at least temporarily be in data exchange with each other, e.g., via a network connection or respective interfaces. Consequently, individual units of the computing unit may be located apart from each other.

Preferably, the computing unit is part of a local hospital information system (HIS) or a radiology information system (RIS) and is adapted to carry out the inventive method for one medical site, e.g. a corresponding medical facility. Alternatively, the computing unit may be realized in the form of a central computing unit communicating with a plurality of medical sites or a plurality of local information systems and be adapted to carry out the inventive method for their respective pluralities of medical imaging modalities.

A further embodiment of the present invention is directed to a computer program product comprising program elements which induce a computing unit of a system for performing at least one medical imaging procedure using an imaging modality, to perform the steps according to at least one embodiment of the inventive method, when the program elements are loaded into a memory of the computing unit, wherein the medical imaging procedure is performed under remote supervision.

A further embodiment of the present invention is directed to a computer-readable medium on which program elements are stored that are readable and executable by a computing unit of a system for performing at least one medical imaging procedure using an imaging modality, in order to perform steps of at least one embodiment of the inventive method, when the program elements are executed by the computing unit, wherein the medical imaging procedure is performed under remote supervision.

The realization of at least one embodiment of the invention by a computer program product and/or a computer-readable medium has the advantage that already existing systems can be easily adopted by software updates in order to work as proposed by embodiments of the invention.

The computer program product can be, for example, a computer program or comprise another element next to the computer program as such. This other element can be hardware, for example a memory device, on which the computer program is stored, a hardware key for using the computer program and the like, and/or software, for example a documentation or a software key for using the computer program. The computer program product may further comprise development material, a runtime system and/or databases or libraries. The computer program product may be distributed among several computer instances.

In summary, at least one embodiment of the present invention enables a change in the daily workflow for medical sites such as radiology departments. At least one embodiment of the present invention centralizes experienced and well-trained technologists/radiographers (expert operators) in at least one, preferably several remote workplaces. At least one embodiment of the invention further improves the distribution of technical/medical expertise of the expert operators especially to regions or locations with no or only little expertise availability. By introducing a matching step, it ensures that high level expertise is provided where needed.

By providing a communication channel, competence and experience of expert operators are remotely connected and shared during an imaging procedure, thus ensuring an increase in image quality, reduction of rescans and long waiting or travel times for patients thus increasing patient comfort. By providing access to an imaging modality as well as other communication channels, a workflow according to at least one embodiment of the present invention includes the following:
- an expert operator is no longer bound to the site of the imaging modality
- local operator-expert operator interaction may take place virtually increase knowledge level
- an expert operator is no longer bound to the full duration of an imaging procedure but may instead attend several imaging procedures at almost the same time.

Figure 1:
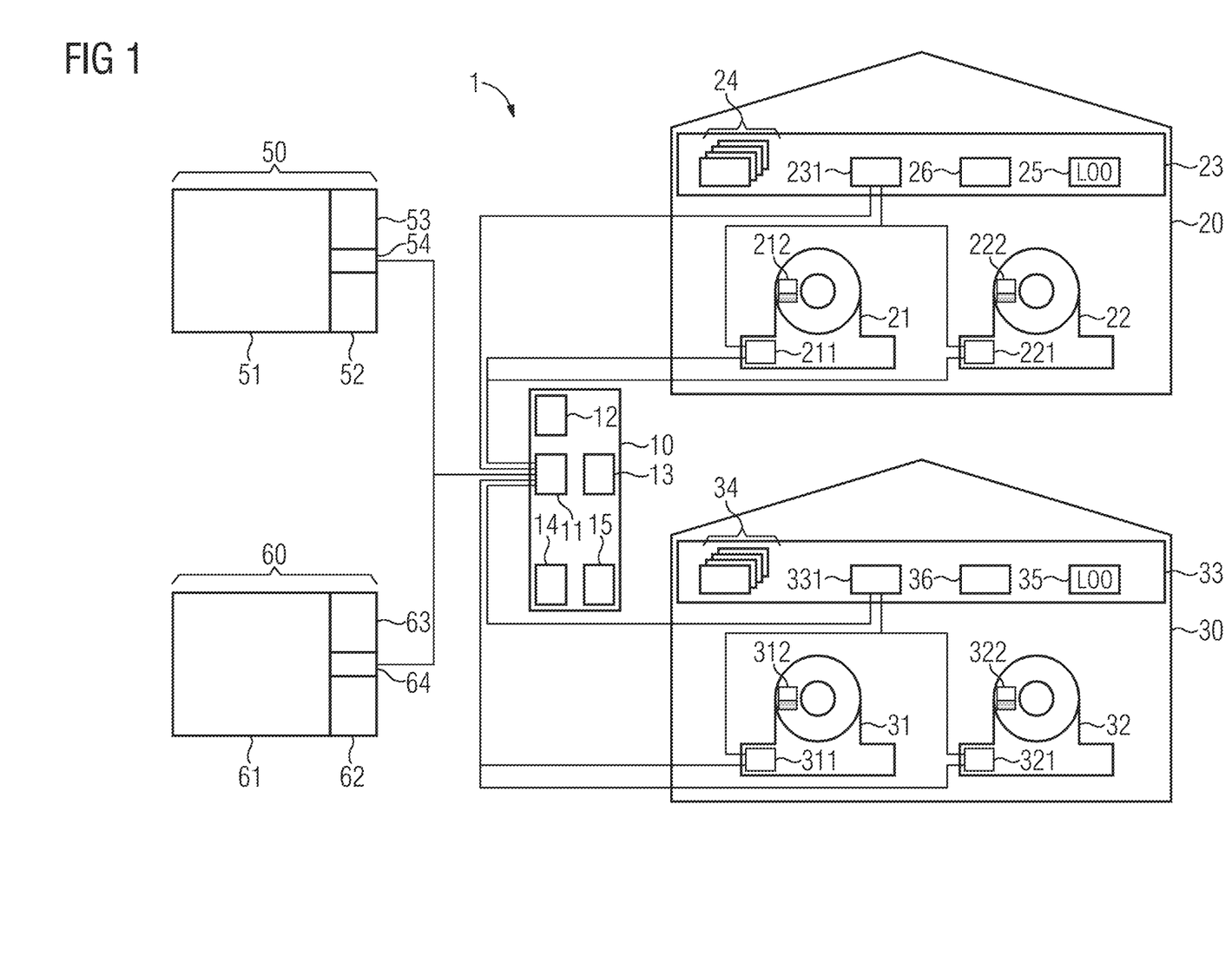
FIG. 1 depicts an inventive system for performing at least one medical imaging procedure according to an embodiment of the present invention.

FIG. 1 depicts a system 1 for performing at least one medical imaging procedure according to an embodiment of the present invention. System 1 is adapted to perform the inventive method according to one or more embodiments of the method, e.g. as further described with respect to FIG. 2. System 1 comprises components and/or units, which may be distributed over a spread environment. Thus, individual system components may be located at different sites or locations. However, there may be system components located at the same site.

The system comprises a computing unit 10. The system 1 further comprises a first remote workplace 50 and a second remote workplace 60. The system 1 further comprises several imaging modalities 21, 22, 31, 32. The system may comprise more than two remote workplaces, but also less. System 1 may comprise more than four imaging modalities, but also less.

Imaging modalities 21, 22 are located in a medical facility 20, e.g. a hospital located at a first site. Imaging modalities 21, 22 may be realized as CT, ultrasound, X-ray (e.g. mammography), angiography or MRT system, however other types of imaging modalities are likewise possible. Imaging modalities 31, 32 are located in a medical facility 30, e.g. an ambulant radiology center located at a second site. Imaging modalities 31, 32 may be realized as CT, ultrasound, X-ray (e.g. mammography), angiography or MRT system, however other types of imaging modalities are likewise possible. Imaging modalities 21, 22, 31, 32 of system 1 are however adapted to generate medical image data as a result of a medical imaging procedure IMP using a respective image generation unit not further described in detail. Imaging modalities 21, 22, 31, 32 further comprise a user interface unit 212, 222, 312, 322 comprising an input and an output unit. The output unit may be adapted to graphically visualize generated image data to a local operator or a patient. The output unit may be adapted to graphically visualize a graphical user interface for planning an imaging procedure or a corresponding protocol. Furthermore, an output unit may be adapted to visualize a chat window enabling written or video communication with a remote expert operator. The output unit may likewise be adapted to output audio chat signals. The input unit may be adapted to receive user input as regards procedure or protocol planning, written or audio chat input or the like. Thus, the user interface units 212, 222, 312, 322 may comprise an LCD, plasma or OLED screen or display. It can also comprise a touch-sensitive screen, a keyboard, a mouse, or a microphone and loudspeaker. Accordingly, the user interface units 212, 222, 312, 322 may further comprise respective processing units (not shown) adapted e.g. for providing a graphical user interface as laid out above, for displaying generated medical image data on the display and/or for processing manual or audio input received from user.

Imaging modalities 21, 22, 31, 32 may further comprise interface units 211, 221, 311, 321 adapted for bi-directional data exchange with the respective processing unit 23, 33, as laid out further below.

Imaging modalities 21, 22, 31, 32, may be located at more or less than two locations or different medical facilities 20, 30.

Medical facilities 20 and 30 each comprise a local processing unit 23 and 33. Local processing units 23, 33 are adapted to collect and store electronic files for patients treated in the respective medical facility 20, 30, e.g. in an electronic patient register 24, 34 comprising a for each patient an electronic health record EHR. Electronic health records EHR are characterized in that they comprise patient related data, i.e. data identifying the patient, data indicative of a medical condition, electronic referral documents, electronic prior report documents, prior or currently suspected diagnosis, a treatment or a medical imaging procedure plan, image data or the like. Local processing units 23, 33 further comprise a local database 25, 35 each comprising data on preferably a plurality of local operators LOO, wherein the data relate to individual local operator persons and the data comprise data identifying the local operator persons, respectively, data indicative of working hours and/or data on technical expertise or an experience level. Electronic patient file register 24, 34 as well as local operators database 25, 35 may be extended, amended or updated (semi)-automatically or manually, e.g. when a new patient or a new local operator is registered to the processing unit 23, 33 or data related to a local operator need to be adjusted. Manual amendments may be conducted via a user interface unit of the processing unit 23, 33 basically corresponding to the user interface unit of the imaging modality 21, 22, 31, 32. Local processing units 23, 33 may further comprise a scheduling unit 26, 36 arranged for scheduling, coordinating or monitoring medical imaging procedures IMP to be performed on any imaging modalities of the respective medical facility 20, 30 in the course of a working shift, a day or a week ahead. With other words, the scheduling units 26, 36 are adapted to provide an electronic schedule or plan SCH. Schedule SCH is adapted to indicate for each imaging modality which patient will receive a medical imaging procedure and the corresponding time. Schedule SCH may be displayed to and/or amended by a user, e.g. a local operator via user interface unit of the processing unit 23, 33.

Local processing units 23, 33 may be implemented as local servers comprising a micro-controller or an integrated circuit. Local processing units 23, 33 may comprise hardware and/or software elements, e.g. a microprocessor or an FPGA (Field Programmable Gate Array). Local processing units 23, 33 may further comprise a memory unit, which may be implemented as temporal storage unit, e.g. a random access memory=RAM or a permanent mass storage unit hard drive, USB-stick, SD-card, solid state or the like.

Local processing units 23, 33 may further comprise an interface unit 231, 331 adapted for bi-directional data exchange with either the respective imaging modalities 21, 22, 31, 32 (via their respective interface units 211, 221, 311, 321). For example, imaging modality 22 may actively send update data on the duration of a current medical imaging procedure IMP to the scheduling unit 26 or the scheduling unit 26 may send data on the next imaging procedure to be performed on imaging modality 21 to this modality. Local processing units 23, 33 may preferably be implemented as a HIS- or RIS-system.

The interface units 211, 221, 311, 321, 231, 331 for data exchange may be realized as hardware- or software-interface, e.g. a PCI-bus, USB or firewire. Data transfer preferably is realized using a network connection. The network may be realized as local area network (LAN), e.g. an intranet or a wide area network (WAN). Network connection is preferably wireless, e.g. as wireless LAN (WLAN or WiFi). The network may comprise a combination of different network examples. Data transfer may be on a request- or push-base.

Workplaces 50, 60 are characterized that they are positioned at a remote location from at least one of the medical imaging modalities 21, 22, 31, 32. This means that a workplace 50, 60 may be realized as a stand-alone service-center remote from any medical facility 20, 30. Alternatively, a workplace 50, 60 may be located in or as integral part of a medical facility 20, 30, e.g. workplace 60 may correspond to an expert/radiology center of medical facility 30. As such, workplace 60 may provide technical/medical expertise as a service to the remote medical facility 20. Workplaces 50, 60 comprise each a respective user interface unit 51, 61 comprising an input and an output unit. The output unit may be adapted to graphically visualize generated image data to an expert operator located and working at the workplace 50, 60. The output unit may be adapted to graphically visualize a graphical user interface for planning an imaging procedure or a corresponding protocol. Furthermore, an output unit may be adapted to visualize a chat window enabling written or video communication with a local operator at the site of an imaging modality 21, 22, 31, 32. The output unit may likewise be adapted to output audio chat signals. The input unit may be adapted to receive user input (of a remote expert operator) as regards logging in to at least one imaging modality, procedure or protocol planning, e.g. adaptation of a protocol parameter, written or audio chat input or the like. Preferably, the output units of the user interface units of the workplaces are adapted to mirror the graphical output of the user interface unit 212, 222, 312, 322. Accordingly, the user interface units 51, 61 may comprise an LCD, plasma or OLED screen or display. They can also comprise a touch-sensitive screen, a keyboard, a mouse, or a microphone and loudspeaker. Processing units 53, 63 of workplaces 50, 60 are adapted e.g. for providing a graphical user interface as laid out above, for displaying generated medical image data on the display and/or for processing manual or audio input received from user and more.

Workplaces 50, 60 further comprise an expert operators' database 52, 62. These databases contain a list of all expert operators EXO working at the workplace 50, 60. The database contains all data available for each expert operator EXO. Data on the expert operator EXO may comprise data identifying an expert operator, availability data (working hours, absences) and data on the technical/medical expertise. With other words, the database 52, 62 provides an expert operators' register.

Databases 52, 62 may be extended, amended or updated (semi-) automatically or manually, e.g. when a new expert operator is registered to a workplace 50, 60 or data related to an expert operator need adjustment. Manual amendments may be conducted via the user interface unit of the respective workplace 50, 60.

Workplaces 50, 60 further comprise an interface unit 54, 64 for data exchange, e.g. for data transfer with at least one of the imaging modalities 21, 22, 31, 32 (i.e. the communication channel), at least one of the processing units 23, 33 or the computing unit 10 of the system 1 as described further below. Interface units 54, 64 and data exchange via the same may be configured the same way as the interface units 211, 221, 311, 321, 231, 331 and data transfer of the imaging modalities 21, 22, 31, 32 or the processing units 32, 33.

Workplaces 50, 60 may be realized comprising stationary workstations comprising local servers and/or databases. However, workplaces may also comprise a mobile device like a tablet for providing the user interface units 51, 61 and interface units 54, 64, while the processing units 63, 53 and the databases 62, 52 may be realized as a local or central server system physically detached from the mobile device. Here, more than one interface unit is provided for each workplace 50, 60.

The computing unit 10 of the system 1 may comprise a server system. The computing unit may comprise a real or virtual group of computers like a so called 'cluster' or 'cloud'. Alternatively, the computing unit may be a central server, e.g. a cloud server, or a local server, e.g. located on a site of a medical facility 20, 30. Computing unit may be realized as part of the processing unit 23 or 33 and may thus be part of a medical facility 20, 30 serving only one or a plurality of medical facilities 20, 30. However, it may likewise be realized as stand-alone entity separate from the medical facilities 20, 30. In particular, computing unit 10 may be realized as virtual machine in the cloud. Like all other system components, the computing unit 10 comprises an interface unit 11. Interface unit 11 is configured to acquire data on at least one medical imaging procedure to be performed, on at least one expert operator or on at least one local expert. The interface unit 11 and corresponding data transfer is configured the same way as already laid out above. Computing unit further comprises a matching unit 12 adapted for matching data on the medical imaging procedure with data on the expert operator and/or the local operator. The computing unit further comprises an assigning unit 13 adapted to assign at least one expert operator and/or local operator to a medical imaging procedure based on the matching. The computing unit further comprises a providing unit 14 adapted to provide, i.e. initiate, e.g. via corresponding notifications to workplaces 50, 60, imaging modalities 21, 22, 31, 32 or processing units 23, 33, at least one communication channel between an imaging modality 21, 22, 31, 32 and a remote workplace 50, 60.

As already indicated above, individual system components may be at least temporarily connected to each other for data transfer and/or exchange. For example, computing unit 10 may be activated on a request-base by any of processing units 23, 33, wherein the request is sent via the interface unit 231, 331. Computing unit 10 further communicates with databases/registers 52, 62, 25, 35, 26, 36, 24, 34 via described interfaces to retrieve data on expert or local operators and planned medical imaging procedures (and/or related patients). Workplaces 50, 60 may request establishment of a communication channel by sending a start notification to at least one of the imaging modalities 21, 22, 31, 32 via interfaces 64, 54 and 211, 221, 311, 321.

Figure 2:
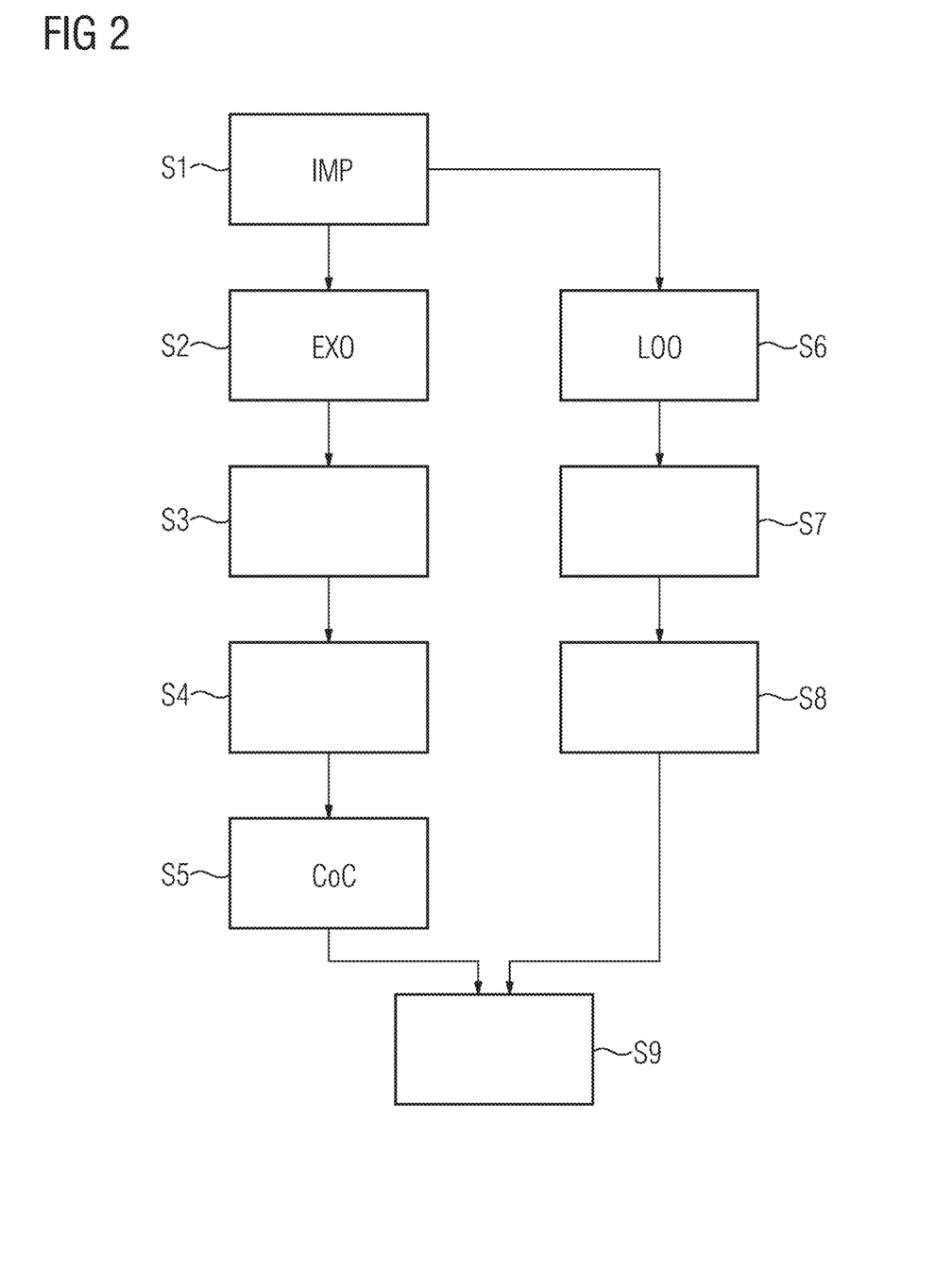
FIG. 2 depicts an inventive method for performing at least one medical imaging procedure according to an embodiment of the present invention.

FIG. 2 depicts an inventive method for performing at least one medical imaging procedure according to an embodiment of the present invention. The inventive method is a computer-implemented method. The inventive method is characterized in that the medical imaging procedure is performed under remote supervision, i.e. expert operator EXO supervision from a remote workplace 50, 60.

In step S1 data on at least one medical imaging procedure IMP to be performed on either one of imaging modalities 21, 22, 31, 32 are acquired. Step S1 may comprise sending a request notification requesting data on the medical imaging procedure to the processing units 23, 24 and receiving data on at least one, preferably more than one imaging procedure IMP from the processing unit 23, 24. Data on the imaging procedure IMP may comprise patient related data, data on body region or organ of interest, initial suspicion data, current medical condition data, data on timing of the imaging procedure and or data on applicable imaging modality, e.g. type and availability. Those data may be provided upon internal request by the processing subunits 24, 34, 26, 36 or the imaging modalities 21, 22, 31, 32 and may be sent to the computing unit 10.

In a step S2 data on at least one expert operator, preferably more than one expert operator EXO, located at a workplace 50, 60 remote from the imaging modality 21, 22, 31, 32 are acquired. Step S2 may likewise comprise sending a request notification requesting data on the expert operator EXO to the workplaces 50, 60 and receiving data on the expert operators EXO from the workplaces 50. 60. Data on the expert operators EXO may comprise identification data, availability data, expert knowledge data. Those data may be provided upon internal request by the databases 52, 62 and may be sent to the computing unit 10 via interfaces 54, 64.

With other words, steps S1 and S2 comprise requesting data from at least one database 24, 34, 52 or 62. Alternatively, data are sent to the computing unit 10 on a push-basis, e.g. automatically upon actualization or amendment of an entry in any of the databases 24, 34, 52 or 62 and at least temporarily stored in a storage unit 15 of the computing unit.

In a step S3 data on the medical imaging procedure IMP are matched with data on the expert operator EXO. Here the matching unit 12 of the computing unit correlates data items related to imaging procedures IMP with data items related to expert operators EXO to determine a conformity measure for each combination or pair of expert operator EXO and imaging procedure IMP. Not all data items provided to the matching unit 12 need to be considered for the matching step. Rather, preset categories or classes of data items relating to an expert operator EXO and to a medical imaging procedure IMP are predefined to be correlated to each other. For example, availability data items for expert operators EXO are correlated to preset time requirement items of an imaging procedure IMP. If the preset time for the imaging procedure IMP lies within working hours of an expert operator EXO, a first conformity measure element is determined. Furthermore, expert operator related data item may correspond to pediatric experience, i.e. experience in imaging children, which often enough impose specific requirements on the imaging setup. An imaging procedure related data item indicating that the patient to be imaged is a child, may thus be correlated to an expert operator related data item stating that the expert operator has a certain experience level with imaging children. Thereby, another conformity measure element is determined. The total number of data items correlated for one expert operator-imaging procedure pair is not limited and depends on the number of available data items relating or applicable to the same data category and which may thus be correlated. Accordingly, the conformity measure may comprise a plurality of individual elements which together construe an overall conformity degree. There may be conformity measure elements, that when below a predefined threshold, prohibit or alternatively cause an assignment of an expert operator EXO to an imaging procedure IMP, irrespective of other determined conformity measure elements.

In step S4 an expert operator EXO is assigned to at least one medical imaging procedure IMP based on the matching. This step comprises identifying the expert operator EXO from the group of considered expert operators, which has the highest conformity measure for a certain imaging procedure IMP. Identification may be based on evaluating the total number of conformity measure elements and/or the individual conformity determined for each element. Assignment of the expert operator EXO to the imaging procedure IMP further comprises introducing or entering a marker or an expert operator tag in the scheduling unit 26, 36 of a medical facility 20, 30, wherein the marker is adapted to identify the assigned expert operator EXO. The introduction of the marker may take place based on a corresponding order notification from the computing unit 10 to the processing unit 23, 33, wherein the order notification comprises data identifying the addressed expert operator-imaging procedure pair. Accordingly, the step of assigning comprises adapting the schedule SCH present in the schedule unit 26, 36.

Figure 3:
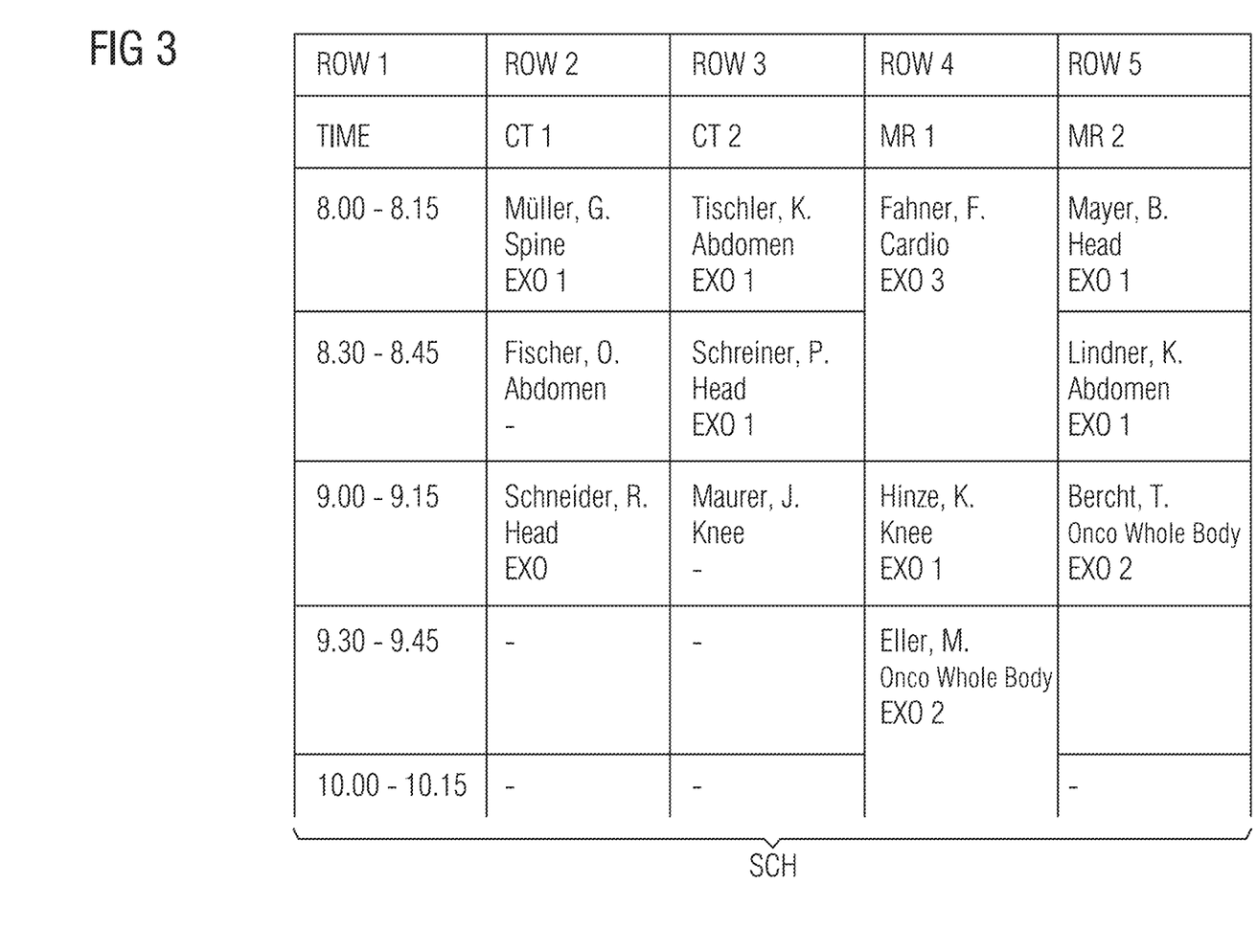
FIG. 3 depicts a schedule as adapted according to an embodiment of the present invention.

FIG. 3 depicts a schedule SCH inventively adapted according to one embodiment. Row 1 (left side) depicts times/durations of imaging procedures. Row 2 to Row 5 represent imaging modalities 21, 22, 31, 32 in a medical facility 20, 30, here comprising CT1, CT2, MR1 and MR2. Of course, more or less and other imaging modalities may be provided in the medical facility. Each line in the schedule SCH stands for a duration of 15 minutes time slots for imaging procedures at the individual imaging modalities. The entries for the imaging procedures each comprise at least the patient name, e.g. Tischler, K., the body region to be imaged, e.g. abdomen, in special cased also the kind of imaging procedure may be indicated here, e.g. oncological or cardio examination, and a further field identifying the expert operator assigned, e.g. EXO1, EXO2 or EXO3. There may likewise be imaging procedures with no expert operator assigned. The imaging procedures do not indicate an expert operator, accordingly. However, these imaging procedures do have a local operator assigned, which may likewise be indicated and recorded in the schedule SCH (not shown).

Step S4 in particular comprises that one expert operator EXO shows a maximum conformity degree for a plurality of imaging procedures IMP. In particular, those imaging procedures IMP are planned basically for the same time. Here, the expert operator EXO is concurrently assigned to more than one imaging procedures IMP as laid out above.

In a further step S5, a communication channel COC between the imaging modality 21, 22, 31, 32 and the remote workplace 50, 60 is provided. Step S5 comprises—after assignment of expert operator EXO to imaging procedure IMP—sending notifications to either the workplace 50, 60 the assigned expert operator EXO is working at and to the imaging modality 21, 22, 31, 32 the imaging procedure IMP shall be performed at, thereby mutually identifying the respective communication partners for the imaging procedure IMP. As soon as the imaging procedure IMP is approaching or has already started, the expert operator EXO may manually initiate by sending access request to the respective imaging modality 21, 22, 31, 32 and logs into the processing system of the imaging modality. Based on the request, furthermore, a chat channel may be established enabling written, or audio communication. Access request may likewise be sent automatically, e.g. triggered by time.

Especially in case, the expert operator is parallelly assigned to more than one imaging procedure, is automatic request sending may be advantageous. In this case, more than one communication channel COC is established parallelly.

As soon as the communication channel COC is established, the user interface unit 51, 61 may mirror for the expert operator EXO a graphical user interface as likewise displayed at the imaging modality 21, 22, 31, 32 for remotely setting or adapting imaging parameters, for slice planning and/or patient positioning via the communication channel in (quasi) real-time. Further the mirrored graphical user interface may enable the expert operator EXO to remotely start/stop image acquisition. In addition, the expert operator may communicate with a local operator LOO present at the imaging modality via audio, textual and or video live chat channel.

The steps of matching, assigning and providing may be repeated for a plurality of expert operator-imaging procedure pairs, wherein the order of the steps is not fixed by the present invention. Ideally, the result of the inventive method is that each imaging procedure planned is assigned a remote expert operator EXO in the corresponding schedule SCH. Alternatively, it may be a result of the inventive method that no expert operator is assigned to a certain imaging procedure IMP (due to unavailability of needed expertise or due to the insight that no remote expertise is needed).

Further method steps S6 to S9 are optional.

In step S6, data on at least one local operator LOO, preferably more than one local operator LOO, located at the medical facility of a respective imaging modality 21, 22, 31, 32 are acquired. Step S6 may likewise comprise sending a request notification requesting data on the local operator LOO to the processing units 23, 33, the local operator databases 25, 35, respectively and receiving data on the local operators LOO therefrom. Data on the local operators LOO may comprise identification data, availability data, technical knowledge data. Those data may be provided upon internal request by the databases 25, 35 and may be sent to the computing unit 10 via interfaces 231, 331.

Thus, also step S6 may comprise requesting data from at least one database 25, 35. Alternatively, data are sent to the computing unit 10 on a push-basis, e.g. automatically upon actualization or amendment of an entry in databases 25, 35 and at least temporarily stored in a storage unit 15 of the computing unit.

In a step S7, data on the medical imaging procedure IMP are matched with data on the local operator LOC. Here the matching unit 12 of the computing unit correlates data items related to imaging procedures IMP with data items related to local operators LOO to determine a conformity measure for each combination or pair of local operator LOO and imaging procedure IMP. Not all data items provided to the matching unit 12 need to be considered for the matching step. Rather, preset categories or classes of data items relating to a local operator LOO and to a medical imaging procedure IMP are predefined to be correlated to each other. For example, availability data items for local operator LOO are correlated to preset time requirement items of an imaging procedure IMP. If the preset time for the imaging procedure IMP lies within working hours of a local operator LOO, a first conformity measure element is determined. Furthermore, a local operator LOO related data item may e.g. correspond to oncologic experience. An imaging procedure related data item indicating that the patient to be imaged has cancer as a prior diagnosis, may thus be correlated to a local operator related data item attesting high level experience in oncology, another conformity measure element is determined. Like with the expert operator EXO matching, the total number of data items correlated for one local operator-imaging procedure pair is not limited and depends on the number of available data items relating or applicable to the same data category and which may thus be correlated. Accordingly, the conformity measure may comprise a plurality of individual elements which all together construe an overall conformity degree. There may be conformity measure elements, that when below a predefined threshold, prohibit an assignment of a local operator LOO to an imaging procedure IMP, irrespective of other determined conformity measure elements.

In step S8 a local operator LOO is assigned to at least one medical imaging procedure IMP based on the matching. This step comprises identifying the local operator LOO from the group of considered local operators LOO, which has the highest conformity measure for a certain imaging procedure IMP. Identification may be based on evaluating the total number of conformity measure elements and/or the individual conformity determined for each element. Steps S4 and S8 may further comprise an evaluation of determined conformity measures of the other operators' group, respectively. Thus, assigning an expert operator EXO to an imaging procedure IMP may comprise evaluating conformity measures of local experts and the other way round. In case of surplus of technical expertise, imaging procedure may be performed without either one of expert and local operator EXO, LOO and only one operator is assigned thus saving valuable working time, which may be spent on another imaging procedure.

Assignment of the local operator LOO to the imaging procedure IMP further comprises introducing or entering a marker or a local operator LOC tag in the scheduling unit 26, 36 of a medical facility 20, 30, wherein the marker is adapted to identify the assigned local operator LOO. The introduction of the marker may take place based on a corresponding order notification from the computing unit 10 to the processing unit 23, 33, wherein the order notification comprises data identifying the addressed local operator-imaging procedure pair. Accordingly, the step of assigning comprises adapting the schedule SCH present in the schedule unit 26, 36.

In optional step S9 an identification tag for the expert operator EXO involved in the imaging procedure IMP is filled with data identifying the expert operator. Typically, generated image data correspond to DICOM standard. Currently generated images will have a DICOM header which does not allow to reflect a distributed setup of two operators (including a remote expert operator). Instead, DICOM standard does currently only cover header fields like 'operator's name' (0008,1070) or 'operator identification sequence' (0008,1072) which trace only one operator. An institution an operator is working for, is currently not captured.

According to step S9, an additional meta data tag or field in the DICOM header could serve to provide a record of the expert operator directly in the image data file. This step corresponds to adhering the assigned expert operator to the generated medical image data. This step supports clear documentation and tracing of the actual operator situation for the imaging procedure in the generated image data. This tagging might e.g. serve to directly assign a previously involved expert operator in a follow-up examination of the same patient. This tagging especially is of interest for setups where the expert operator is not an employee of the medical facility, where an imaging procedure is conducted on a patient. Accordingly, in addition to the expert operator tag, further tags might be introduced to the DICOM image header, e.g. 'second/remote institution name' (0008,0083), 'second/remote institution address' (0008,0084), 'second/remote institution code sequence' (0008,0085).

In summary, at least one embodiment of the present invention is based on the insight, that technical and/or medical expertise does not need to be present in a scanner environment but may be provided remotely. By connecting expert operators to remote medical facilities, expert operators can still guide an imaging procedure. Expert operators can even connect to multiple imaging modalities at the same time and guide multiple imaging procedures. Advantageously, expert operators are scheduled for and assigned to more than one imaging procedure in parallel according to the needs defined by the complexity of the planned imaging procedure. Of course, local operator capacities at the medical sited are advantageously considered, too.

The inventive setup of at least one embodiment thus provides technical and/or medical expertise as a service based on a specific demand.

At least one embodiment of the present invention realizes an efficient and thus cost- and time-saving solution for planning and assigning expert operators of at least one remote workplace to preferably more than one imaging procedure at one or a plurality of medical sites. This corresponds to high-level expert resource management, decreasing personnel costs and increasing services to patients as well as medical facilities and optimizes device and personnel utilization. The inventive rule-based computing unit may be inserted as an add-on/plug-in software/hardware module into existing hospital or radiology scheduling systems or as software/hardware extension to modality and patient planning solutions. Preferably, the rule-based matching and assigning steps may be manually configured, e.g. to further optimize modality utilization.

Some rules are provided as examples, which may be likewise connected:
- if IMP data item is: MR CARDIO EXAM>>assign LOCAL OPERATOR 3 only (as local operator 3 data item is: high level cardio exam experience)
- if IMP data item is: MR ONCO EXAM>>assign EXPERT OPERATOR 1 (as expert operator 1 data item is: high level onco exam experience)
- if IMP data item is: CT EXAM>>assign LOCAL OPERATOR 1 (for educational purposes of new operators, as local operator 1 data item is: high level CT EXAM expertise)
- if IMP data item is: MR EXAM and local operator data item is: low MR EXAM experience>>assign EXPERT OPERATOR 4 (as expert operator 4 data item is: high level MR EXAM expertise)
- if IMP data item is: MR ONCO EXAM planned for MR scanner 1>>assign EXPERT OPERATOR 2 (as expert operator 2 data item is: high level onco exam experience) AND set IMP data item of next MR ONCO imaging procedure to a new, later timepoint including n minutes delay (as MR ONCO EXAM is usually complex and thus time consuming)
- if IMP data item is CT EXAM and TRAUMA>>assign EXPERT OPERATOR 5 (as expert operator 5 data item is: on-demand CT expertise)

At least one embodiment of the inventive setup increases the modality and personnel utilization and thereby increase examination throughput with less resources and accelerate amortization of medical devices.

Wherever meaningful, individual embodiments or their individual aspects and features can be combined or exchanged with one another without limiting or widening the scope of the present invention. Advantages which are described with respect to one embodiment of the present invention are, wherever applicable, also advantageous to other embodiments of the present invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for performing at least one medical imaging procedure using an imaging modality, the medical imaging procedure being performed under remote supervision, the computer-implemented method comprising:
   acquiring, with a computing unit, data on the medical imaging procedure to be performed;
   acquiring, with the computing unit, data on at least one expert operator located at a workplace remote from the imaging modality;
   matching, with the computing unit, the data on the medical imaging procedure acquired with the data on the at least one expert operator acquired;
   assigning, with the computing unit, at least one expert operator to the medical imaging procedure based on the matching;
   providing a communication channel between the imaging modality and the remote workplace;
   acquiring, with the computing unit, data on at least one local operator located at a site of the imaging modality;
   matching the data on the medical imaging procedure with the data on the at least one local operator;
   determining a conformity degree based on a total number of items of the data on the at least one local operator that match the medical imaging procedure; and
   assigning the at least one local operator to the medical imaging procedure based on the conformity degree being greater than or equal to a desired threshold;
   wherein the communication channel enables the at least one assigned expert operator to remotely perform the medical imaging procedure.

2. The computer-implemented method of claim 1, wherein the providing of the communication channel comprises notifying, with the computing unit, the imaging modality of the at least one expert operator assigned, based upon the assigning.

3. The computer-implemented method of claim 1, wherein the at least one expert operator is concurrently assigned to more than one imaging procedure and wherein a communication channel is provided between the remote workplace and each respective imaging modality of the at least one expert operator assigned.

4. The computer-implemented method of claim 1, wherein the data on the at least one expert operator comprises at least one of:
   identification data,
   availability data, and
   expert knowledge data.

5. The computer-implemented method of claim 1, wherein the data on the at least one medical imaging procedure comprise at least one of:
   patient related data,
   data on the respective imaging modality,
   data on body region or organ of interest,
   initial suspicion data,
   current medical condition data, and
   data on timing of the imaging procedure.

6. The computer-implemented method of claim 1, wherein the data on the at least one local operator comprises at least one of:
   identification data, availability data, or expert knowledge data.

7. The computer-implemented method of claim 1, wherein the communication channel between imaging modality and remote workplace enables at least one of remote setting of imaging parameters at the imaging modality by the at least one expert operator and at least one of verbal and written communication via the imaging modality and the remote workplace.

8. The computer-implemented method of claim 1, wherein the assigning of the at least one expert operator is adhered to the medical image data generated with the imaging procedure.

9. The computer-implemented method of claim 1, wherein the acquiring data on the medical imaging procedure and on at least one expert operator comprises requesting data from at least one database.

10. The computer-implemented method of claim 3, wherein the more than one imaging procedure are performed at least two different medical sites.

11. A system for performing at least one medical imaging procedure using an imaging modality, the at least one medical imaging procedure being performed under remote supervision, the system comprising:

at least one imaging modality;

at least one workplace remote from the imaging modality; and a computing unit configured for acquiring data on the medical imaging procedure to be performed, acquiring data on at least one expert operator located at a workplace remote from the at least one imaging modality, matching data acquired on the medical imaging procedure with data acquired on the at least one expert operator, assigning at least one expert operator to the medical imaging procedure based on the matching, wherein the at least one imaging modality and the remote workplace are further configured to provide a communication channel between each other, acquiring, with the computing unit, data on at least one local operator located at a site of the imaging modality;

matching the data on the medical imaging procedure with the data on the at least one local operator;

determining a comformity degree based on a total number of items of the data on the at least one local operator that match the medical imaging procedure; and assigning the at least one local operator to the medical imaging procedure based on the conformity degree being greater than or equal to a desired threshold;

wherein the communication channel enables the at least one assigned expert operator to remotely perform the medical imaging procedure.

12. A non-transitory computer program product storing program elements to induce a computing unit of a system, for performing at least one medical imaging procedure using an imaging modality, to perform the method of claim 1 when the program elements are loaded into a memory of the computing unit.

13. A non-transitory computer-readable medium storing program elements that are readable and executable by a computing unit of a system, for performing at least one medical imaging procedure using an imaging modality, to perform the method of claim 1, when the program elements are executed by the computing unit.

14. The computer-implemented method of claim 2, wherein the at least one expert operator is concurrently assigned to more than one imaging procedures and wherein a communication channel is provided between the remote workplace and each respective imaging modality of the at least one expert operator assigned.

15. The computer-implemented method of claim 2, wherein the assigning of the at least one expert operator is adhered to the medical image data generated with the imaging procedure.

16. The computer-implemented method of claim 2, wherein the acquiring data on the medical imaging procedure and on at least one expert operator comprises requesting data from at least one database.

17. The computer-implemented method of claim 1, wherein the imaging modality includes at least one first user interface, a graphical output of the at least one first user interface configured to be mirrored to at least one second user interface at the remote workplace.

* * * * *